US00PP11926P2

(12) United States Plant Patent
Swift

(10) Patent No.: US PP11,926 P2
(45) Date of Patent: Jun. 12, 2001

(54) VERBENA PLANT NAMED 'SHAUNA ANN'

(75) Inventor: Scott W. Swift, Gilman, IL (US)

(73) Assignee: David Paul Eastburn, Chalfont, PA (US)

( * ) Notice: Subject to any disclaimer, the term of this patent is extended or adjusted under 35 U.S.C. 154(b) by 0 days.

(21) Appl. No.: 09/320,194

(22) Filed: May 26, 1999

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Melissa L. Kimball

(57) ABSTRACT

A new cultivar of Verbena named 'Shauna Ann' as characterized by its hardiness in Zone 4 combined with lavender-pink fragrant flowers, finely incised foliage, and a compact growth habit.

1 Drawing Sheet

BACKGROUND OF THE INVENTION

The present invention relates to a new and distinct cultivar of an interspecific Verbena hybrid and will be referred to hereafter by the cultivar name 'Shauna Ann', 'Shauna Ann' represents a new hardy Verbena, a perennial grown for landscape use.

The new cultivar was discovered by the inventor; in a garden in Laurel, Iowa in 1987. 'Shauna Ann' was selected from plants grown from seed collected from *Verbena canadensis* plants. It was chosen as unique for its combined qualities of foliage, habit, flower color and fragrance, and hardiness. Hardiness was a substantial selection factor as it survived and thrived under Zone 4 garden locations for ten years.

Asexual reproduction of the new cultivar, using cuttings, was first accomplished by the inventor at Swift Greenhouses in Gilman, Iowa in May of 1998. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish this cultivar from other commercial varieties.

1. 'Shauna Ann' is hardly in Zone 4. *Verbena canadensis* is short-lived in Zone 5 and there are no commercially grown Verbenas that are known to be hardy in Zone 4. Most are hardy to Zone 9.
2. 'Shauna Ann' has fragrant, lavender-pink flowers.
3. 'Shauna Ann' has a compact growth habit, reaching a height of 12 to 15 cm and a spread of 38 to 45 cm. Typically, Garden Verbena cultivars have spreads of 60 to 100 cm.
4. 'Shauna Ann' has more finely incised foliage than typical for *Verbena canadensis* and cultivars such as *Verbena canadensis*'Homestead Purple'.

BRIEF DESCRIPTION OF THE DRAWING

The photograph is of a 5 month old plant produced by growing three rooted cuttings in a one gallon container for 20 weeks under greenhouse conditions in Chalfont, Pa. The foliage and habit are well depicted in the photograph. The flower color is as close as reasonably possible by conventional photography.

BOTANICAL DESCRIPTION OF THE PLANT

The following is a detailed description of the new cultivar as grown in a one-gallon container for 5 months under greenhouse conditions. General characteristics of the new cultivar were recorded after observing plants under garden conditions for 2 years in Chalfont, Pa. Phenotypic differences may be observed with variations in environmental, climatic, and cultural conditions. The color determination is in accordance with The R.H.S. Colour Chart of The Royal Horticultural Society, London, England, except where general color terms of ordinary dictionary significance are used.

Botanical classification: 'Shauna Ann' is an interspecific hybrid of Verbena of unknown parentage. *Verbena canadensis* is a likely parent because of its hardiness (Zone 5) and because it was derived from a seed package labeled as such. The finely divided leaves, the longevity of the plant and its dense plant habit are uncharacteristic of *Verbena canadensis*. These characteristics are more indicative of selections of *Verbena×hybrida* and *Verbena teniusecta* that are only hardy to Zone 9, therefore indicating an interspecific origin.

Commercial classification: Garden Verbena

General characteristics:

*Blooming period.*—May or June to frost; dependent on environmental conditions.
*Plant habit.*—Low spreading, good basal branching, deliquescent (irregular).
*Plant height.*—12–15 cm.
*Plant spread.*—38–45 cm.
*Hardiness.*—Zone 4.
*Type.*—Perennial herb.
*Root system.*—Fibrous.
*Fragrance.*—Strongly fragrant (hyacinth-like).
*Propagation.*—Stem cuttings.
*Resistance.*—No unusual susceptibility or resistance to pests and insects known to date.

Stems:

*Shape.*—Tetragonal.
*Color.*—146B with purple overlay (187A) on mature stems.
*Size.*—2 mm on average (Peduncle 1.5 mm).

*Internodes.*—1–1.8 cm.

*Surface.*—Sericeous (long, soft, appressed, non-glandular hairs).

Leaves:

*Arrangement.*—Decussate.

*Type.*—Simple.

*Shape.*—Ovate.

*Base.*—Cuneate.

*Tip.*—Acuminate.

*Venation.*—Not prominent.

*Margins.*—Parted, typically tripartate (further incised).

*Attachment.*—Petiolate.

*Surface.*—Sericeous (sparsely).

*Color.*—Upper surface 137B, Lower Surface 138B.

*Size.*—Up to 4.5 cm in length, 2.8 cm in width.

Inflorescence:

*Type.*—Indeterminant.

*Form.*—Corymb.

*Perianth.*—*Salverform.*

*Corolla.*—Zygomorphic, sympetalous, 5 lobed; 3 lobes are 6–7 mm in length with single notch, 3–5.5 mm in width, 2 lobes are 6–7 mm in length (no notch), 2.5–3 mm in width, Color is 78A (fades to 78C).

*Calyx.*—Gamosepalous, 8 mm long, 1 mm wide, color is 146B.

*Reproductive organs.*—4 stamens (didynamous, included, adnate to petals), 1 style with superior ovary.

COMPARISON WITH OTHER CULTIVARS

The new cultivar 'Shauna Ann' is hardier than any Garden Verbena known to the inventor in commerce. The cultivar Verbena×'Taylor Town Red' (U.S. Plant Pat. No. 9,270) is hardy to Zone 6, however most cultivars have a rating to Zone 9. Both 'Taylor Town Red' and *Verbena canadensis* 'Homestead Purple' (unpatented) are not as compact, have less finely divided leaves, and a pubescent surface to the leaves. *Verbena canadensis* does not have longevity and is a short-lived perennial under most conditions and spreads to 60 cm. Verbena× 'Shauna Ann' also differs from the hybrid cultivars that are grown as ground cover types. They can typically spread to 90 cm with a trailing growth habit, whereas the spread of 'Shauna Ann' is under 45 cm and has a compact growth habit under the conditions that it has been tested.

I claim:

1. A new and distinct cultivar of Verbena plant named 'Shauna Ann' as described and illustrated.

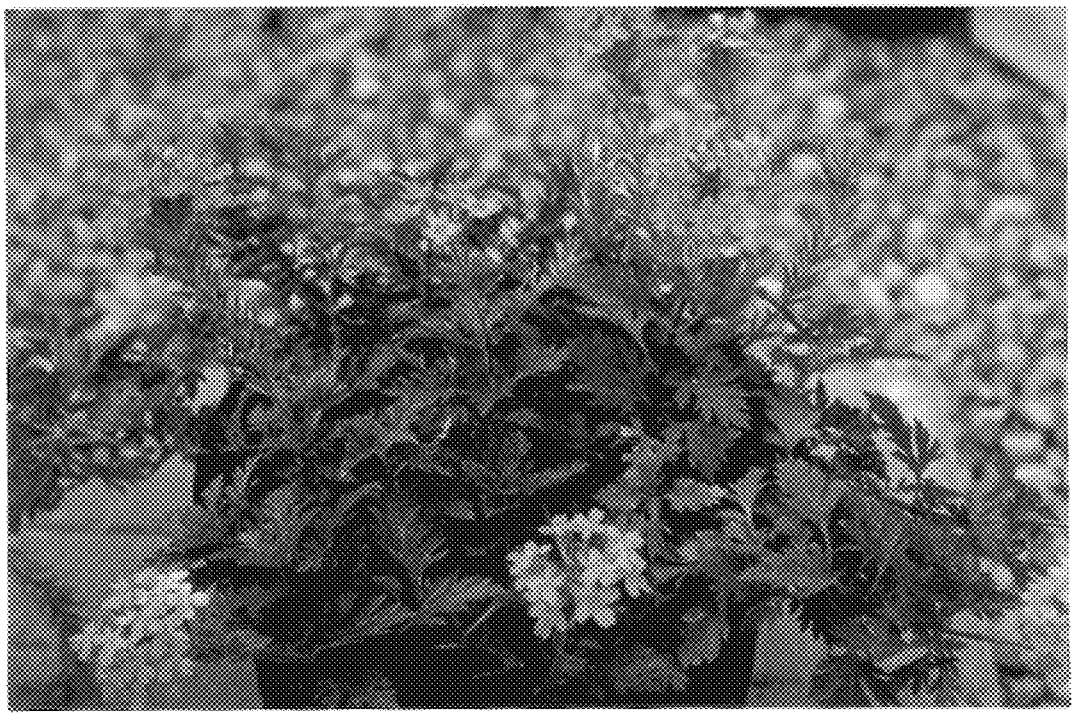

* * * * *